(12) United States Patent
Choi et al.

(10) Patent No.: US 10,806,603 B2
(45) Date of Patent: Oct. 20, 2020

(54) METHOD FOR WALKING ASSIST AND DEVICE OPERATING THE SAME

(71) Applicant: Samsung Electronics Co., Ltd., Suwon-si, Gyeonggi-do (KR)

(72) Inventors: Byung-Kwon Choi, Seongnam-si (KR); Keehong Seo, Seoul (KR); Youngbo Shim, Seoul (KR); Taesin Ha, Seongnam-si (KR); Seungyong Hyung, Yongin-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 538 days.

(21) Appl. No.: 15/412,562

(22) Filed: Jan. 23, 2017

(65) Prior Publication Data

US 2018/0064560 A1    Mar. 8, 2018

(30) Foreign Application Priority Data

Sep. 5, 2016    (KR) .......................... 10-2016-0113849

(51) Int. Cl.
    *G06F 19/00*    (2018.01)
    *A61F 2/70*    (2006.01)
    (Continued)

(52) U.S. Cl.
    CPC .............. *A61F 2/70* (2013.01); *A61B 5/112* (2013.01); *A61F 2/68* (2013.01); *A61H 3/00* (2013.01);
    (Continued)

(58) Field of Classification Search
    CPC ...... A61F 2/68; A61F 2/70; A61F 2/64; A61F 2/72; A61F 5/00; A61F 5/0102; A61F 5/02; A61H 3/00; A61H 2230/625; A61H 2230/065; A61H 2201/5084; A61H 2201/5069; A61H 2201/501; A61H 2201/1676; A61H 2201/165; A61H 2201/1628; A61H 1/0244; A61H 2201/5007; A61H 2201/5079; A61H 2201/164; A61H 1/024; A61H 2201/1215; A61H 2201/5061; A61H 2003/007; A61H 2201/1207; A61H 2201/5064; A61H 2201/5097; A61H 1/0266; A61H 2201/1238; A61H 2201/1246; A61H 2201/1261; A61H 2201/149; A61H 2201/1642; A61H 2230/605; A61H 3/008; A61H 1/0255; A61H 1/0262; A61H 2201/1463; A61H 2201/1481; A61H 2201/1652; A61H 2201/1664; A61H 2201/1671; A61H 2201/5002;
    (Continued)

(56) References Cited

U.S. PATENT DOCUMENTS 7,353,986 B2 * 4/2008 Sugai ................... G01C 22/006
                                                        235/105
7,549,969 B2 * 6/2009 van den Bogert .... A61F 5/0102
                                                        602/16

(Continued)

*Primary Examiner* — Khoi H Tran
*Assistant Examiner* — B M M Hannan
(74) *Attorney, Agent, or Firm* — Harness, Dickey and Pierce, P.L.C.

(57) ABSTRACT

Disclosed is a walking assist method including acquiring arm motion data; creating walking data based on the arm motion data; and assisting a walking based on the created walking data.

18 Claims, 10 Drawing Sheets

(51) Int. Cl.
*A61B 5/11* (2006.01)
*A61F 2/68* (2006.01)
*A61H 3/00* (2006.01)
*A61H 1/02* (2006.01)
*A61B 5/024* (2006.01)
*A61B 5/107* (2006.01)
*A61B 5/00* (2006.01)

(52) U.S. Cl.
CPC ............ *A61B 5/024* (2013.01); *A61B 5/1071* (2013.01); *A61B 5/7203* (2013.01); *A61B 5/7235* (2013.01); *A61H 1/0244* (2013.01); *A61H 2201/165* (2013.01); *A61H 2201/1628* (2013.01); *A61H 2201/1676* (2013.01); *A61H 2201/501* (2013.01); *A61H 2201/5069* (2013.01); *A61H 2201/5084* (2013.01); *A61H 2230/065* (2013.01); *A61H 2230/625* (2013.01)

(58) Field of Classification Search
CPC ........ A61H 2201/5092; A61H 2205/10; A61H 2230/60; A61H 1/00; A61H 1/0274; A61H 1/0277; A61H 1/0281; A61H 2001/0211; A61H 2201/0107; A61H 2201/1223; A61H 2201/1614; A61H 2201/1616; A61H 2201/1619; A61H 2201/1623; A61H 2201/163; A61H 2201/5028; A61H 2201/5035; A61H 2201/5048; A61H 2201/5058; A61H 2230/40; A61H 2230/62; A61H 3/02; A61B 5/112; A61B 5/1071; A61B 5/024; A61B 5/7235; A61B 5/7203; A61B 2562/0219; A61B 5/1121; A61B 5/1038; A61B 5/1123; A61B 2503/40; A61B 2562/0252; A61B 5/0002; A61B 5/0022; A61B 5/04888; A61B 5/11; A61B 5/1112; A61B 5/1122; A61B 5/1124; A61B 5/1126; A61B 5/1127; A61B 5/4836; A61B 5/6812; A61B 5/6823; A61B 5/6828; A61B 5/721; B25J 9/0006; B25J 9/1694; G01C 22/006; G01C 21/12; G01C 21/16; G01C 21/165; G01C 21/206; A63B 2024/0071; A63B 2024/0096; A63B 2071/0644; A63B 2071/0647; A63B 2071/065; A63B 2071/0661; A63B 2220/40; A63B 2225/50; A63B 24/0062; A63B 24/0087; A63B 69/0035; A63B 71/0619; B62D 57/032; G01P 13/00; G01P 15/00; G06F 19/00; G06F 1/163; G06F 1/3206; G06F 1/3218; G06F 1/3234; G06F 1/3265; G06F 1/3287; G06F 1/3296; G06F 3/014; G06F 3/017; G06K 9/00342; G06K 9/00543; G16H 40/67; H04W 4/027; Y10S 901/01

USPC ........................................................ 700/245
See application file for complete search history.

(56) References Cited

U.S. PATENT DOCUMENTS

| | | | |
|---|---|---|---|
| 8,142,371 B2 | 3/2012 | Ikeuchi et al. | |
| 9,351,900 B2* | 5/2016 | Walsh | B25J 9/0006 |
| 9,610,208 B2* | 4/2017 | Kazerooni | A61H 3/00 |
| 10,048,087 B2* | 8/2018 | Nakajima | A61B 5/112 |
| 10,234,293 B2* | 3/2019 | Matsushita | G01C 21/16 |
| 10,427,293 B2* | 10/2019 | Asbeck | B25J 9/0006 |
| 10,434,030 B2* | 10/2019 | Asbeck | A61H 3/00 |
| 2006/0149420 A1* | 7/2006 | Ikeuchi | B62D 57/032 700/245 |
| 2007/0061038 A1* | 3/2007 | Takenaka | B62D 57/032 700/245 |
| 2009/0131839 A1* | 5/2009 | Yasuhara | A61F 5/0102 601/5 |
| 2010/0132464 A1* | 6/2010 | Yasuhara | A61B 5/1038 73/504.12 |
| 2011/0131005 A1* | 6/2011 | Ueshima | A63B 24/0062 702/141 |
| 2011/0205067 A1* | 8/2011 | Konishi | A61H 3/008 340/573.1 |
| 2013/0131555 A1* | 5/2013 | Hook | A61B 5/112 600/595 |
| 2013/0138394 A1* | 5/2013 | Shiga | G01C 22/006 702/160 |
| 2013/0158444 A1* | 6/2013 | Herr | A63B 21/00181 601/23 |
| 2013/0237884 A1* | 9/2013 | Kazerooni | A61H 1/0244 601/34 |
| 2014/0024981 A1 | 1/2014 | Chun et al. | |
| 2014/0278220 A1* | 9/2014 | Yuen | G01B 21/16 702/150 |
| 2015/0088269 A1* | 3/2015 | Roh | A61H 3/00 623/25 |
| 2015/0134080 A1 | 5/2015 | Roh | |
| 2015/0173993 A1* | 6/2015 | Walsh | B25J 9/0006 414/4 |
| 2015/0224013 A1* | 8/2015 | Kwon | A61H 1/0262 482/51 |
| 2015/0265428 A1 | 9/2015 | Akiba | |
| 2016/0000635 A1 | 1/2016 | Miyake | |
| 2016/0018872 A1* | 1/2016 | Tu | G06F 1/3234 345/173 |
| 2016/0029928 A1 | 2/2016 | Jang et al. | |
| 2016/0051435 A1* | 2/2016 | Ito | A61H 3/00 623/24 |
| 2016/0107309 A1* | 4/2016 | Walsh | A61H 3/00 248/550 |
| 2016/0250094 A1* | 9/2016 | Amundson | A61H 1/0244 623/24 |
| 2016/0262969 A1* | 9/2016 | Ohta | A61H 1/0255 |
| 2016/0331560 A1* | 11/2016 | Tong | A61H 3/00 |
| 2017/0027803 A1* | 2/2017 | Agrawal | A61B 5/224 |
| 2017/0128293 A1* | 5/2017 | Tsusaka | A61G 5/00 |
| 2019/0049479 A1* | 2/2019 | Malhotra | A61B 5/11 |

* cited by examiner

METHOD FOR WALKING ASSIST AND DEVICE OPERATING THE SAME

CROSS-REFERENCE TO RELATED APPLICATION

This application claims under 35 U.S.C. § 119 to Korean Patent Application No. 10-2016-0113849, filed on Sep. 5, 2016, in the Korean Intellectual Property Office, the entire contents of which are incorporated herein by reference in their entirety.

BACKGROUND

1. Field

At least one example embodiment relates to a walking assist method and/or a device that performs the walking assist method.

2. Description of the Related Art

With the onset of rapidly aging society, an increasing number of persons may experience inconvenience and/or agony from joint issues and, therefore, there is interest in a walking assist device that may assist seniors or patients having joint issues with walking. In addition, walking assist devices for strengthening muscle for the military purpose and the like are being developed.

For example, a walking assist device may include a body frame configured to mount to a torso of a user, a pelvis frame configured to couple with a lower side of the body frame and wrap around a pelvis of the user, a femoral frame configured to mount to a femoral region of the user, a calf frame configured to mount to a calf region of the user, and a foot frame configured to mount to a foot portion of the user. The pelvis frame and the femoral frame may be connected to be rotatable by way of a hip joint portion, and the calf frame and the foot frame may be connected to be rotatable by way of a wrist joint portion.

SUMMARY

Some example embodiments relate to a method of assisting a walking operation

In some example embodiments, the method may include acquiring, by a controller, arm motion data; generating, by the controller, walking data based on the arm motion data; and assisting, by the controller, the walking operation based on the walking data.

Other some example embodiments relate to a walking assistance device.

In some example embodiments, the device may include a receiver configured to acquire arm motion data; a controller configured to generate walking data based on the arm motion data; and a driver configured to assist a walking operation based on the walking data.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of the present disclosure.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which example embodiments belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Various example embodiments will now be described more fully with reference to the accompanying drawings in which some example embodiments are shown. In the drawings, the thicknesses of layers and regions are exaggerated for clarity.

Hereinafter, example embodiments will be described with reference to the accompanying drawings.

Figure 1:
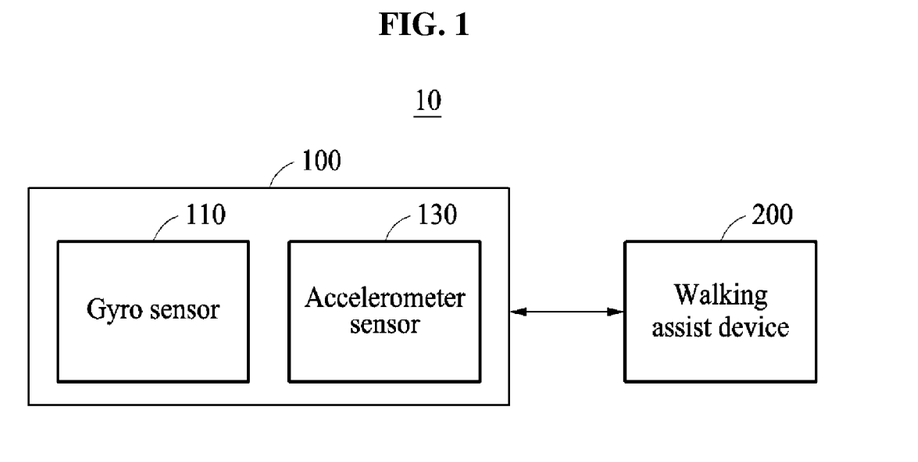
FIG. 1 illustrates a walking assist system according to at least one example embodiment.

FIG. 1 illustrates a walking assist system according to at least one example embodiment.

Referring to FIG. 1, a walking assist system or a gait assist system 10 may include an electronic device 100 and a walking assist device or a gait assist device 200.

The walking assist system 10 may be a system that assists a target object in walking and/or exercising using the electronic device 100 and the walking assist device 200. Here, the target object, that is, a user may refer to, for example, a human being, an animal, a robot, a walking object, an exercising object, and the like, and is not particularly limited thereto. The target object and the user may be interchangeably used throughout.

The electronic device 100 may be, for example, a mobile device. The mobile device may include, for example, a laptop computer, a mobile phone, a smart phone, a tablet personal computer (PC), a mobile Internet device (MID), a personal digital assistant (PDA), an enterprise digital assistant (EDA), a digital still camera, a digital video camera, a portable multimedia player (PMP), a personal navigation device or a portable navigation device (PND), a handheld game console, an e-book, and/or a smart device.

The smart device may include, for example, a smart watch, a smart band, and/or a smart ring. That is, the electronic device 100 may be a wearable device wearable by the user.

The electronic device 100 may communicate with the walking assist device 200 over a communication network. For example, the communication network may be an Internet communication network, an Intranet, a local area network (LAN), a wireless LAN, Bluetooth, including Bluetooth low energy (LE), and and/or wireless fidelity (Wi-Fi) based on an Institute of Electrical and Electronics Engineers (IEEE) 802.11 standard. The electronic device 100 may transmit and receive data to and from the walking assist device 200 in real time over the communication network.

The electronic device 100 may include an inertial measurement unit (IMU), for example, a gyro sensor 110 and/or an accelerometer sensor 130.

The electronic device 100 may generate arm motion data using the gyro sensor 110 and/or the accelerometer sensor 130. For example, the electronic device 100 may generate arm motion data based on angular velocity data created at the gyro sensor 110 and/or acceleration data created at the accelerometer sensor 130. The arm motion data may include at least one of the angular velocity data and the acceleration data. For clarity of description, the angular velocity data may also be referred to gyro data.

The gyro sensor 110 may generate gyro data that is proportional to a rotary velocity or an angular velocity occurring in response to a motion of the gyro sensor 110. The gyro sensor 110 may be an angular velocity measurement sensor configured to measure an angular velocity with respect to X axis, Y axis, and Z axis. Also, the gyro sensor 110 may measure an angular value corresponding to a motion of the user and a heading direction of the user.

The accelerometer sensor 130 may determine the motion of the user by measuring a direction of force based on acceleration occurring in response to a motion of the accelerometer sensor 130. For example, the user may move with holding the electronic device 100 in hand or wearing the electronic device around an arm, and the accelerometer sensor 130 may generate acceleration data in response to a motion of the electronic device 100. The acceleration data may include acceleration information about X axis, Y axis, and Z axis.

Although FIG. 1 illustrates that the gyro sensor 110 and the accelerometer sensor 130 are included in the electronic device 100, example embodiments are not limited thereto. For example, the gyro sensor 110 and/or the accelerometer sensor 130 may outside the electronic device 100. For example, the user may wear or carry at least one of the gyro sensor 110 and the accelerometer sensor 130 around an arm portion, and the walking assist device 200 may directly communicate with at least one of the gyro sensor 110 and the accelerometer sensor 130. Also, while the gyro sensor 110 and the accelerometer sensor 130 are illustrated as separate configurations in FIG. 1, the gyro sensor 110 and the accelerometer sensor 130 may be configured as part of the same inertial measurement device.

Although not illustrated, in addition to the gyro sensor 110 and the accelerometer sensor 130, the electronic device 100 may further include an electromyogram (EMG) sensor, a heart rate sensor, and/or a global positioning system (GPS) sensor to determine a location of the user.

The walking assist device 200 may assist the user having some issues with walking and/or exercise by acquiring arm motion data from the electronic device 100. Therefore, the walk assist system 10 may utilize the gyro sensor 110 and/or the accelerometer sensor 130 integrated into the electronic device 100 rather than a discrete gyro sensor and/or accelerometer integrated into the walking assist device 200. Therefore, the walk assist system 10 may reduce the costs associated with the walking assist device 200 and/or increase the usability of the same.

For example, the walking assist device 200 may generate walking data based on the arm motion data. Here, the walking assist device 200 may generate walking data based on valid data extracted from the arm motion data. The valid data may indicate significant data acquired by eliminating noise data from the arm motion data.

The walking assist device 200 may create an assist torque profile based on the walking data and may create an assist force or an assist torque based on the assist torque profile. The walking assist device 200 may assist the user in walking using the assist torque.

The walking assist device 200 may acquire arm motion data from the electronic device 100 that is an external device, may generate the walking data for assisting a walking, and may assist the user in walking. Also, the walking assist device 200 may efficiently generate the walking data by performing preprocessing on the arm motion data.

Figure 2:
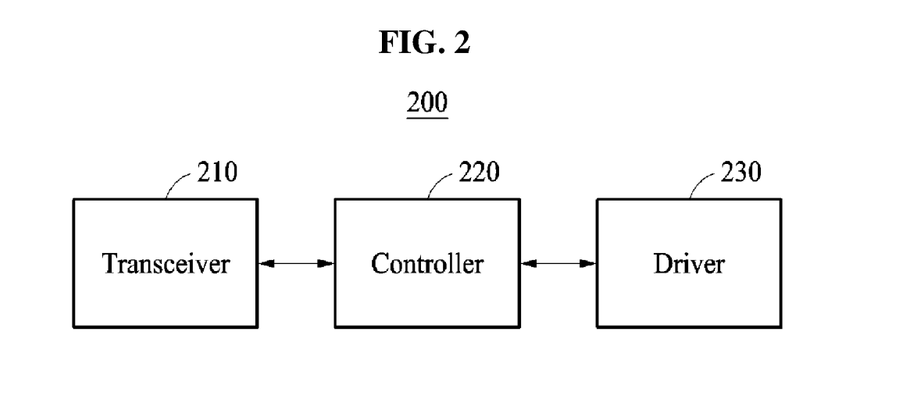
FIG. 2 illustrates a walking assist device of FIG. 1 according to at least one example embodiment.
Figure 3:
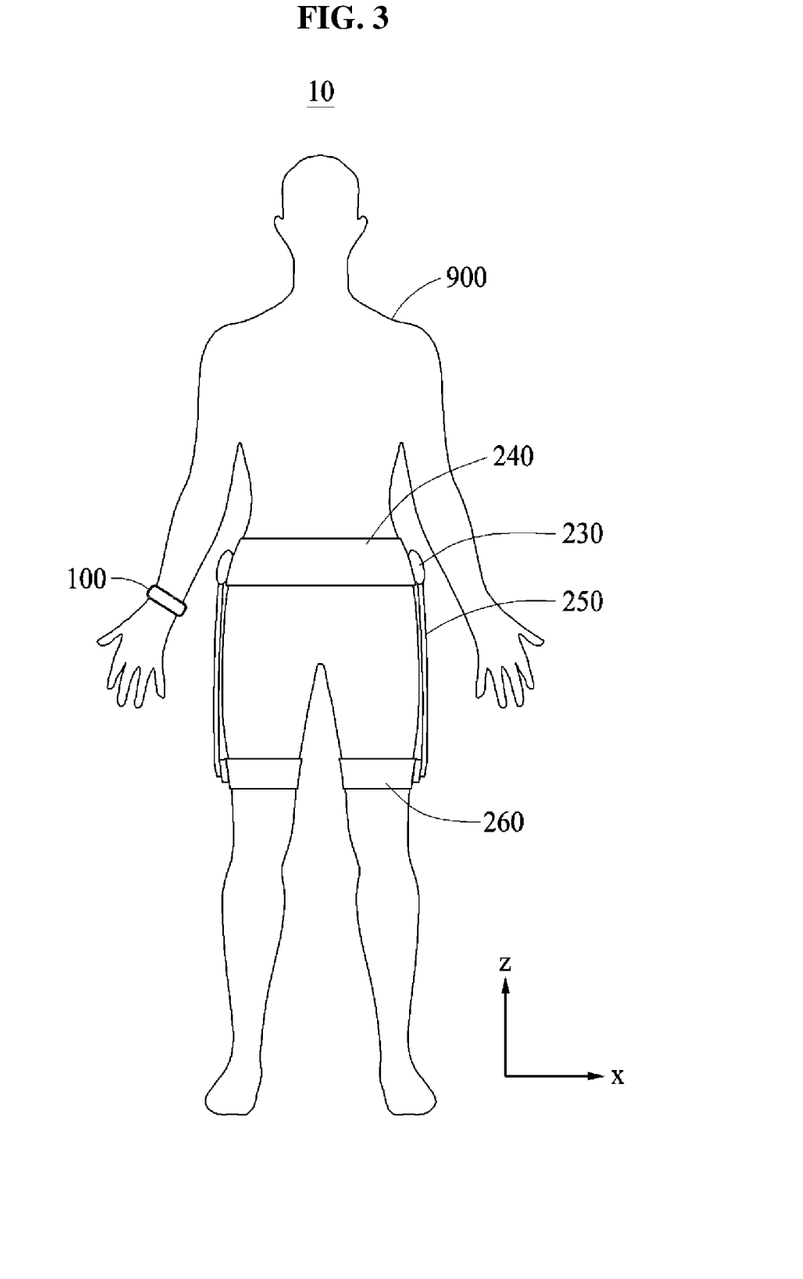
FIG. 3 is a front view illustrating a state in which a user wears an electronic device and the walking assist device of FIG. 1 according to at least one example embodiment.
Figure 4:
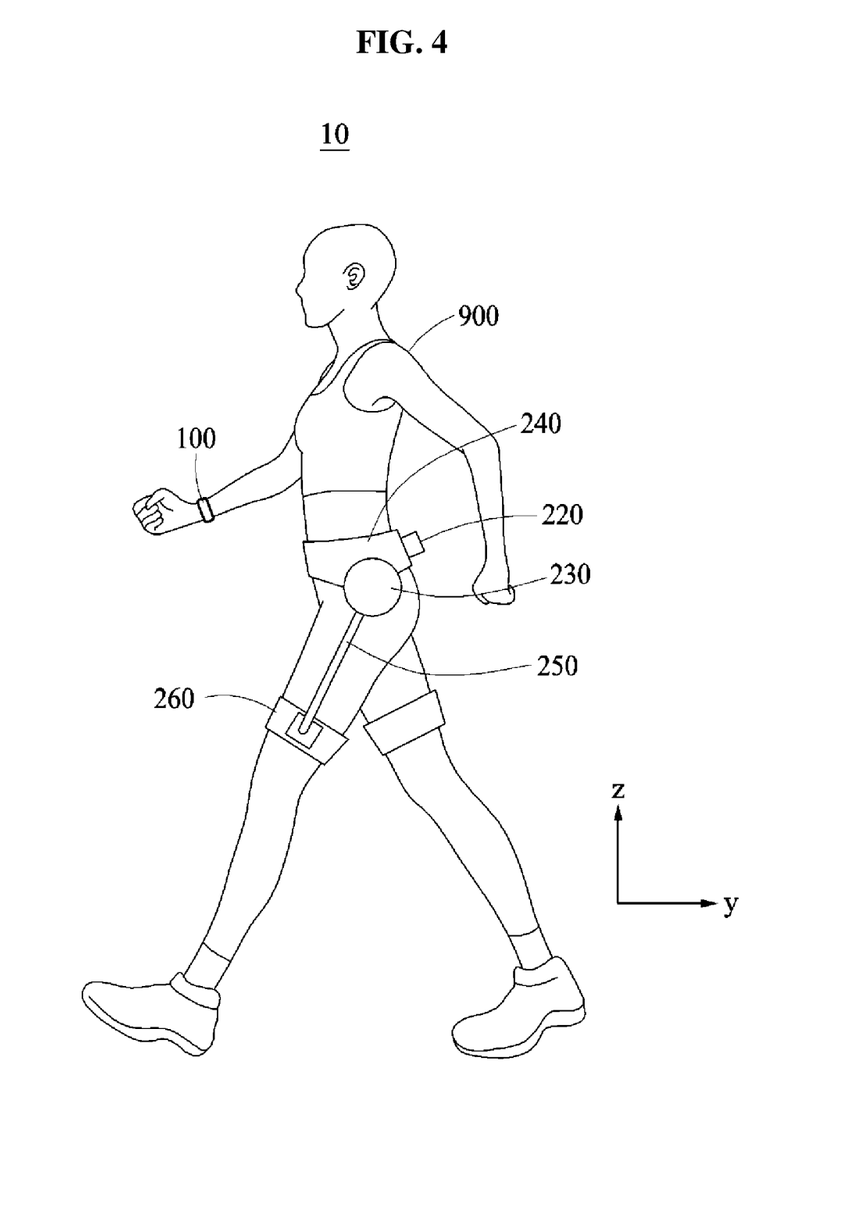
FIG. 4 is a side view illustrating a state in which the user wears the electronic device and the walking assist device of FIG. 1 according to at least one example embodiment.

FIG. 2 illustrates a walking assist device of FIG. 1 according to at least one example embodiment, FIG. 3 is a front view illustrating a state in which a user wears an electronic device and the walking assist device of FIG. 1 according to at least one example embodiment, and FIG. 4 is a side view illustrating a state in which the user wears the electronic device and the walking assist device of FIG. 1 according to at least one example embodiment.

Referring to FIGS. 1 through 4, a target object, for example, a user 900 may wear the electronic device 100 and the walking assist device 200. That is, the electronic device 100 and the walking assist device 200 may be worn by the user 900 and may assist the user 900 in walking and/or exercise.

The electronic device 100 may measure an arm motion of the user 900 using at least one of the gyro sensor 110 and the accelerometer sensor 130, and may generate the arm motion data based on the arm motion.

The arm motion data may include gyro data and/or acceleration data. The gyro data may include coordinates and angular velocity with respect to X axis, Y axis, and Z axis, and the acceleration data may include coordinates and acceleration with respect to X axis, Y axis, and Z axis, in response to an operation of the user 900 that moves an arm.

The walking assist device 200 may receive the arm motion data from the electronic device 100, may generate the walking data for assisting a walking based on the arm motion data, and may assist the user 900 with walking.

The walking assist device 200 may assist the user 900 in walking and/or exercise using another part of an upper body, such as a hand, an upper arm, a forearm, etc., of the user 900, or another part of a lower body, such as a leg, a foot, a calf, a thigh, etc., of the user 900. That is, the walking assist device 200 may assist the user 900 in walking and/or exercise using a portion of the body.

The walking assist device 200 may include a transceiver 210, a controller 220, and a driver 230. The walking assist device 200 may further include a fixing member 240, a power transfer member 250, and a support member 260.

The transceiver 110 may include a transmitting device having hardware and any necessary software for transmitting signals including, for example, data signals and control signals, and a receiving device having hardware and any necessary software for receiving signals including, for example, data signals and control signals.

The transceiver 110 may exchange data with the electronic device 100. For example, the transceiver 210 may receive arm motion data from the electronic device 100.

The controller 220 may include any device capable of processing data including, for example, an application application-specific integrated circuit (ASIC) configured to carry out specific operations based on input data, or a microprocessor configured as a special purpose processor by executing instructions included in computer readable code. The computer readable code may be stored on, for example, a memory (not shown). As discussed in more detail below with reference to FIG. 5, the computer readable code may configure the controller 220 to perform the operations of a preprocessor 221, a walking assist controller 223 and/or an assist torque generator 225.

The controller 220 may control the overall operation of the walking assist device 200. For example, the controller 220 may control the driver 230 to output power for assisting the user 900 in walking. The power may indicate an assist force or an assist torque.

Also, the controller 220 may generate the walking data based on the motion arm data from the electronic device 100, and to control the driver 230 to assist the user 900 in walking and/or exercise based on the walking data. Here, the controller 220 may acquire valid data by performing preprocessing on the arm motion data and may generate the walking data based on the valid data. An operation of the controller 220 that controls walking assist based on the arm motion data is further described with reference to FIG. 5.

The driver 230 may drive a hip joint of the user 900 and may be positioned on a right hip portion and/or a left hip portion of the user 900. For example, the driver 230 may include a motor configured to generate a rotary torque.

The driver 230 may generate an assist force or an assist torque to assist the user 900 in walking under control of the controller 220, for example, as an output of an assist torque profile starts. The assist force or the assist torque may be set by the controller 220 or may be set at an outside.

The fixing member 240 may be fixed to a portion, for example, a waist, of the user 900. The fixing member 240 may be in contact with at least a portion of the outer surface of the user 900. The fixing member 240 may be provided to wrap around the outer surface of the user 900. In some example embodiments, the fixing member 240 may include a belt.

The power transfer member 250 may be connected between the driver 230 and the support member 260. The power transfer member 250 may transfer the power transferred from the driver 230 to the support member 260. For example, the power transfer member 250 may be a lengthwise member, such as a frame, a wire, a cable, a string, an elastic band, a spring, a belt, a chain, and the like.

The support member 260 may support a support target of the user 900, for example, a thigh of the user 900. The support member 260 may be disposed to wrap around at least a portion of the user 900. The support member 260 may apply a force to the support target of the user 900 with the power transferred from the power transfer member 250.

Referring to FIGS. 3 and 4, for clarity of description, the electronic device 100 is worn around a wrist of the user 900 and operates. However, it is provided as an example only and the electronic device 100 may be worn around at least a portion of or all of an arm, for example, an elbow, a finger, an upper arm, a forearm, etc., of the user 900. Also, the user 900 may hold or carry the electronic device 100 with the hand of the user 900, and the electronic device 100 may operate while being held or carried in the hand. That is, the electronic device 100 may be worn by the user 100 in various types of forms.

Although the walking assist device 200 is illustrated herein in a hip type, it is provided as an example only. The walking assist device 200 may be provided to a portion of or all of an upper body, such as a hand, an upper arm, a forearm, etc., of the user 900 or a portion of or all of a lower body, such as a foot, a calf, etc., of the user 900. Also, the walking assist device 200 may be provided to support up to a knee or an ankle in the example of supporting a portion of the lower body, or to support a whole body of the user 900.

Figure 5:
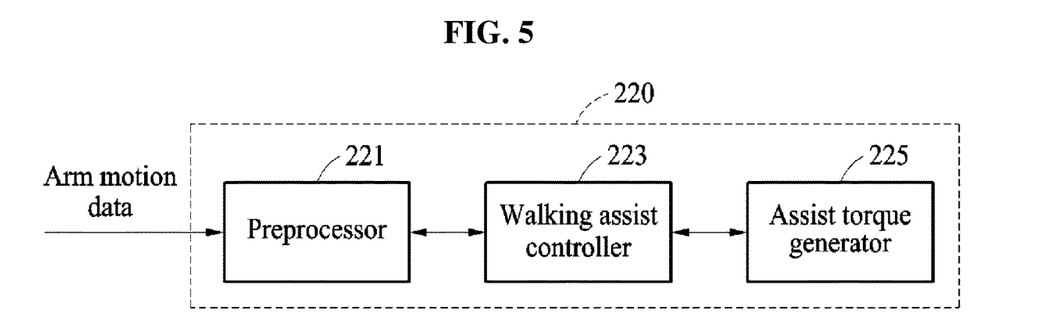
FIG. 5 illustrates a controller of FIG. 2 according to at least one example embodiment.

FIG. 5 illustrates the controller 220 of FIG. 2 according to at least one example embodiment.

Referring to FIG. 5, the controller 220 may include a preprocessor 221, a walking assist controller 223, and an assist torque generator 225. For example, the controller 220 may be programmed with instructions that configure the controller 220 as a special purpose computer to perform the operations of the preprocessor 221, the walking assist controller 223, and the assist torque generator 225.

The preprocessor 221 may perform preprocessing on arm motion data. For example, the preprocessor 221 may extract data that matches a walking direction of the user 900 from the arm motion data. The preprocessor 221 may eliminate or filter out noise data and/or invalid data or insignificant data from the arm motion data.

For example, the user 900 may swing an arm through the air, that is, move an arm forward and backward. Noise data and/or invalid data may be inserted into the arm motion data during a process in which a direction of the arm of the user 900 switches from forward to backward or from backward to forward. Accordingly, the assist provided from the walking assist device 200 may be insignificant to the user 900 without reducing (or, alternatively, eliminating) the noise data and/or the invalid data.

The noise data may refer to data of a direction different from the walking direction of the user 900. The noise data may include high frequency data. The high frequency data may be a high frequency component compared to an arm motion of the user 900 that is employed for general walking.

For example, the preprocessor 221 may eliminate high frequency data from arm motion data and generate the walking data by filtering the arm motion data based on at least one of norm data and a magnitude of a vector of the arm motion data. The arm motion data may include at least one of gyro data and acceleration data. The gyro data may include information associated with an angular velocity of an arm of the user 900 in a vector form, and the acceleration data may include information associated with acceleration of the arm of the user 900 in a vector form.

The norm data may a vector magnitude acquired by adding up a plurality of vectors. For example, norm data of a plurality of vectors $(\vec{A1}, \vec{A2}, \vec{A3})$ may be $\sqrt{|A1|^2+|A2|^2+|A3|^2}$.

As another example, the preprocessor 221 may generate the walking data based on the arm motion data by filtering the arm motion data based on a maximum threshold and a minimum threshold.

The maximum threshold and the minimum threshold used to eliminate the noise data may be input from the user 900. The maximum threshold and the minimum threshold may be preset default values. Also, the maximum threshold and the minimum threshold may be thresholds with respect to an axis.

The preprocessor 221 may generate the walking data by eliminating data greater than the maximum threshold and/or less than the minimum threshold from the arm motion data.

The invalid data may refer to arm motion data that is acquired in a situation in which a walking assist is not required, for example, a situation in which the user 900 does not move, that is, is stopped, a situation in which a significant change in a walking speed occurs, and the like.

The preprocessor 221 may filter out the invalid data or the insignificant data using a sensor (not shown) of the walking assist device 200. For example, the sensor of the walking assist device 200 may sense a motion of a leg of the user 900. The preprocessor 221 may determine whether walking assist is to be provided to the user 900 based on a result of sensing the motion of the leg, and, if the walking assist is not required, may filter the acquired arm motion data.

Also, if the arm motion data is data associated with one arm, for example, a forward direction, the preprocessor 221 may create arm motion data of the other arm, for example, a backward direction by adjusting a balance.

The preprocessor 221 may perform preprocessing on the arm motion data and the walking assist device 200 may be robust against a recognition error and may smoothly switch a walking assist direction instead of suddenly switching the walking assist direction.

The walking assist controller 223 may generate the walking data based on the arm motion data, for example, the preprocessed arm motion data. For example, the walking assist controller 223 may create walking data based on a direction vector. As another example, the walking assist controller 223 may generate the walking data based on an eigenvalue that is created through a principal component analysis (PCA). The eigenvalue may be a characteristic value or root associated with an eigenvector. A walking data creation operation of the walking assist controller 223 will be further described with reference to FIGS. 6 and 7.

The walking assist controller 223 may update the arm motion data to reduce a data error occurring due to a communication delay between the electronic device 100 and the walking assist device 200. For example, the walking assist controller 223 may update the arm motion data by applying a gyro modulation and/or a linear correction scheme to the arm motion data. A walking data updating operation of the walking assist controller 223 will be further described with reference to FIGS. 8, 9A, and 9B.

The walking assist controller 223 may correct an assist torque profile that is created based on the walking data in response to a motion of a leg of the user 900. The motion of the leg of the user 900 may be sensed at the sensor (not shown) of the walking assist device 200. For example, the sensor may use an accelerometer sensor, a gyro sensor, a terrestrial magnetic sensor, etc. In addition, any type of sensors capable of recognizing a motion may be applied. The motion of the leg may be based on an angle of the leg. The angle of the leg may include at least one of a hip angle, a knee angle, and an ankle angle.

If the arm motion data currently being acquired at the transceiver 210 differs from pre-collected arm motion data, the walking assist controller 223 may determine that a current state of the user 900 is abnormal and may suspend or terminate the walking assist.

For example, in abnormal situations, such as a situation in which the user 900 falls down, a situation in which the user 900 suspends walking and/or exercise, a situation in which the user 900 misses the foot, a situation in which the user 900 encounters an accident, and the like, the transceiver 210 may receive arm motion data different from the pre-collected arm motion data. The walking assist controller 223 may suspend or terminate the walking assist.

The walking assist controller 223 may extract a maximum angular velocity value of a walking direction of the user 900 from gyro data, and may normalize an assist force based on the maximum angular velocity value. For example, if the maximum angular velocity value of the walking direction of the user 900 is 5, the walking assist controller 223 may normalize the assist force to 10. That is, the walking assist controller 223 may control the driver 230 to output a value corresponding to two folds of the maximum angular velocity value as the assist force.

The walking assist controller 223 may set the assist force to be different based on a walking and/or exercise environment of the user 900. For example, if the user 900 walks on the level ground, the walking assist controller 223 may set the assist force to be 10. If the user 900 goes up the stairs, the walking assist controller 223 may set the assist force to be 14. If the user 900 goes down the stairs, the walking assist controller 223 may set the assist force to be 5.

The walking assist controller 223 may also set an assist torque profile based on a heart rate of the user 900. The electronic device 100 may measure the heart rate of the user 900 using a heart rate sensor (not shown) and may transmit the measured heart rate to the walking assist device 200. The heart rate sensor may be included in the electronic device 100; however, example embodiments are not limited thereto. Here, the walking assist controller 223 may set the assist force to increase in response to an increase in the heart rate of the user 900, and may set the assist force to decrease in response to a decrease in the heart rate of the user 900.

Also, the walking assist controller 223 may set the assist force to be different for each location based on GPS information of the user 900. The electronic device 100 may measure GPS information of the user 900 using a GPS sensor (not shown), and may transmit the measured GPS information to the walking assist device 200. The GPS sensor may be included in the electronic device 100; however, example embodiments are not limited thereto. For example, if the user 900 is in a dangerous area, the walking assist controller 223 may set the assist force to be output at a relatively low value.

The walking assist controller 223 may set the assist force to be different depending on whether the user 900 walks on an uphill road or walks on a downhill road. The walking assist controller 223 may determine whether the user 900 walks on the uphill road or the downhill road based on the arm motion data currently being acquired.

For example, if a motion angle of an arm of the user 900 leans forward or if a motion of the arm is relatively great in arm motion data, the walking assist controller 223 may determine that the user 223 walks on the uphill road and may set the assist torque profile so that a relatively great assist force may be output. Also, if a motion angle of the arm of the user 900 leans backward or if a motion of the arm is relatively small in the arm motion data, the walking assist controller 223 may determine that the user 900 walks on the downhill road and may set the assist torque profile so that a relatively small assistance force may be output.

The assist torque generator 225 may generate the assist torque profile of the user 900 and may assist the user 900 in walking and/or exercise. For example, the assist torque profile may be generated in advance and may be stored in a memory (not shown). Here, the memory may be provided inside or outside the assist torque generator 225.

The assist torque generator 225 may start an output of the assist torque profile under control of the walking assist controller 223. For example, if the user 900 wears the electronic device 100 around a left arm of the user 900 and stretches the left arm forward, the assist torque generator 225 may output a flexion assist torque profile to a right leg of the user 900 and may output an extension assist torque profile to a left leg of the user 900. Also, if the user 900 stretches the left arm backward, the assist torque generator 225 may output an extension assist torque profile to the right leg and a flexion assist torque profile to the left leg. That is, the assist torque generator 225 may output the extension assist torque profile to a leg that is on the same side of a stretching arm and may output the flexion assist torque profile to a leg that is on the opposite side of the stretching arm.

The assist torque generator 225 may output the flexion assist torque profile to the leg that is on the same side of the stretching arm and may output the extension assist torque profile to the left that is on the opposite side of the stretching arm based on an input of the user 900.

Also, the assist torque generator 225 may adjust a walking assist timing using a delay or an offset parameter. For example, in response to receiving a perfect offset from the user 900, the assist torque generator 225 may assist the user 900 in walking using the left arm and the left leg.

The assist torque generator 225 may correct walking assist balance based on a balance between the right and the left limbs. For example, if imbalance is detected in walking and/or exercise of right and left legs during walking and/or exercising of the user 900, the assist torque generator 225 may assist the user 900 in walking using the balance. That is, the assist torque generator 225 may correct the balance between the right and the left limbs based on the output assist force and a time interval between leg motions of the user 900.

The assist torque generator 225 may also assist the user 900 with walking and/or exercise of a single leg. Also, the assist torque generator 225 may provide only the extension assist torque profile to the user 900 having difficulty in an extending operation and may provide only the flexion assist torque profile to the user 900 having difficult in an flexing operation.

Figure 6:
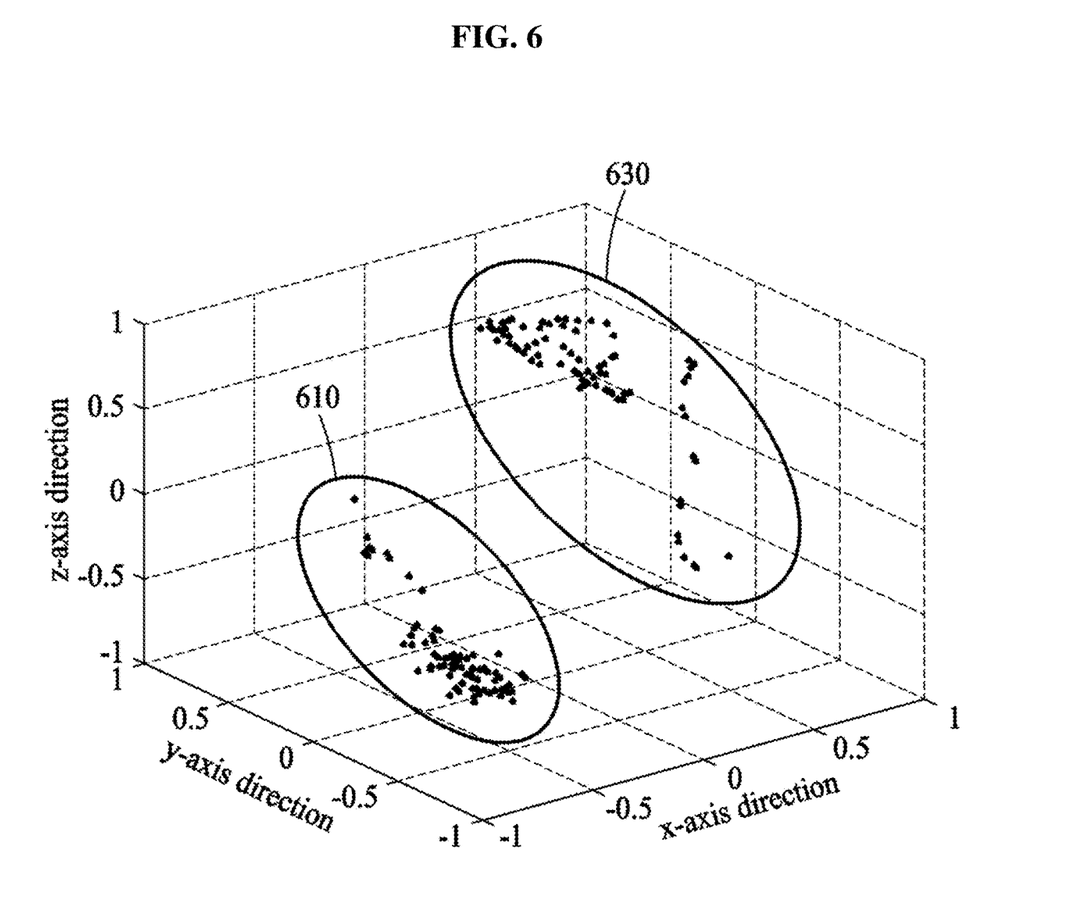
FIG. 6 illustrates an example of an operation of creating, at a walking assist controller of FIG. 5, walking data according to at least one example embodiment.

FIG. 6 illustrates an example of an operation of creating, at the walking assist controller 223 of FIG. 5, walking data according to at least one example embodiment.

Referring to FIG. 6, the walking assist controller 223 may generate the walking data based on gyro data included in the arm motion data, for example, preprocessed arm motion data. The gyro data may be acquired from the electronic device 100 and may be expressed as shown in FIG. 6.

The walking assist controller 223 may use pre-collected arm motion data to generate the walking data. For example, the walking assist controller 223 may acquire gyro data during a desired (or, alternatively, a predetermined) period of time. The walking assist controller 223 may extract a plurality of direction vectors and magnitudes from the gyro data acquired during the period of time. The plurality of direction vectors and magnitudes may be values about angular velocity according to a motion of the arm of the user 900.

The walking assist controller 223 may classify the plurality of direction vectors into a first group 610 and a second group 630 based on a direction. Each of the first group 610 and the second group 630 may be a set of data having similar directions. A direction may be a forward direction or a backward direction. For example, the first group 610 may be a backward direction group and the second group 630 may be a forward direction group. In the first group 610, many direction vectors may be positioned in the backward direction. In the second group 630, many direction vectors may be positioned in the forward direction.

The walking assist controller 223 may calculate an average of direction vectors of each of the first group 610 and the second group 630. The walking assist controller 223 may calculate the average of direction vectors of the first group 610 and the average of direction vectors of the second group 630.

The walking assist controller 223 may determine a first representative direction vector of the first group 610 and a second representative direction vector of the second group 630 based on the average of direction vectors of the first group 610 and the second group 630. A representative direction vector may indicate a representative value about the walking direction of the user 900, and may be a forward direction vector or a backward direction vector. For example, the first representative direction vector may be the backward direction vector and the second representative direction vector may be the forward direction vector.

If all of the first representative direction vector and the second representative direction vector are the forward direction vector or the backward direction vector, the walking assist controller 223 may determine that the current state of the user 900 is abnormal and may suspend or terminate a walking assist.

In some example embodiments, the walking assist controller 223 may generate the walking data by performing an inner product on the first representative direction vector, the second representative direction vector, and preprocessed arm motion data currently being acquired. That is, the walking assist controller 223 may calculate a magnitude of a current walking direction of the user 900 by performing an inner product on the first representative direction vector and the preprocessed arm motion data currently being acquired and by performing an inner product on the second representative direction vector and the preprocessed arm motion data currently being acquired.

Alternatively, in other example embodiments, the walking assist controller 223 may generate the walking data based on norm data of the preprocessed arm motion data instead of performing the inner product. Here, the walking assist controller 223 may also use norm data of pre-collected arm motion data or the first representative direction vector of the first group 610 and the second representative direction vector of the second group 630.

Figure 7:
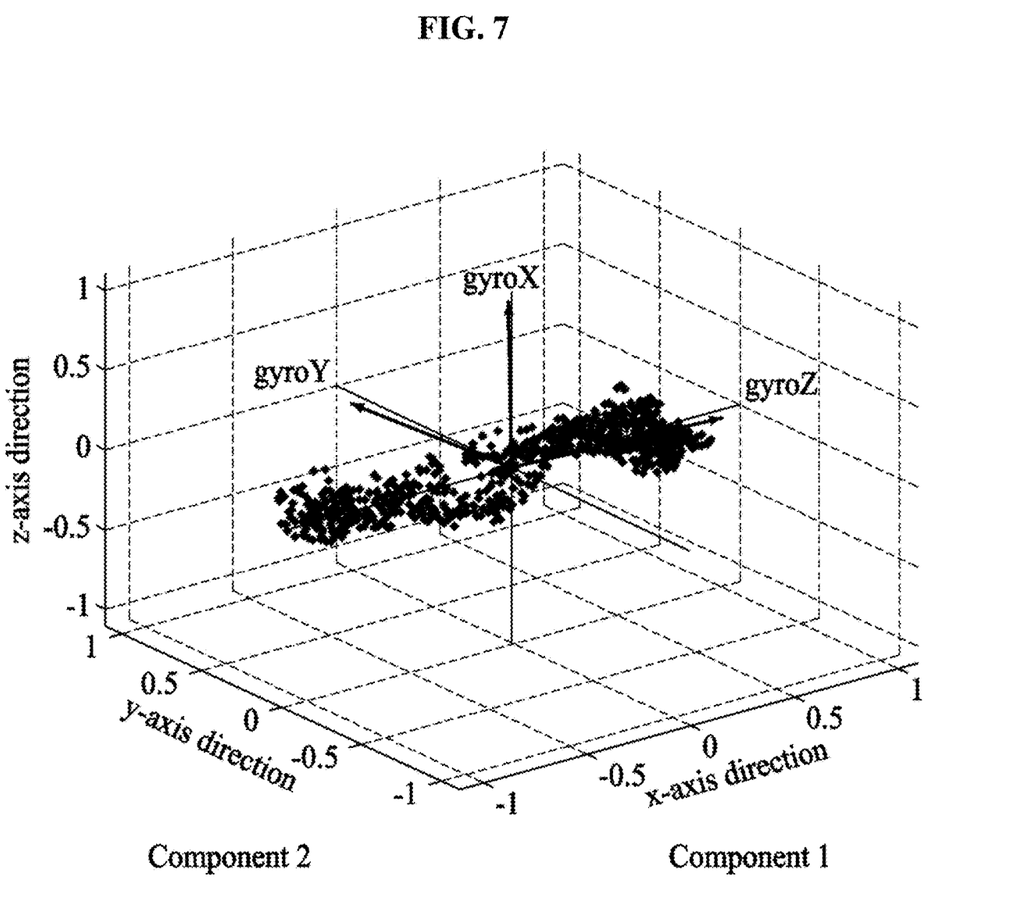
FIG. 7 illustrates another example of an operation of creating, at the walking assist controller of FIG. 5, walking data according to at least one example embodiment.

FIG. 7 illustrates another example of an operation of creating, at the walking assist controller 223 of FIG. 5, walking data according to at least one example embodiment.

Referring to FIG. 7, the walking assist controller 223 may generate the walking data based on an eigenvalue that is created through the principle component analysis (PCA).

The walking assist controller 233 may perform the PCA, which is a technique used to emphasize variation and bring out strong patterns in a dataset by performing an orthogonal transformation to convert the data set into a set of values of linearly uncorrelated variables called principal components.

The walking assist controller 223 may use pre-collected arm motion data to generate the walking data. For example, the walking assist controller 223 may create at least one of an axis, for example, gyroX, gyroY, and gyroZ, of arm motion data pre-collected through the PCA, an eigenvalue, and an eigenvector.

The walking assist controller 223 may determine a walking direction of the user 900 based on an eigenvector having a largest eigenvalue in the pre-collected arm motion data. Here, the walking assist controller 223 may determine a left/right assist strength of an assist torque profile based on the set walking direction.

Also, the walking assist controller 223 may generate at least one of an axis of arm motion data currently being acquired, an eigenvalue, and an eigenvector. The walking assist controller 223 may determine the walking direction of the user 900 based on an eigenvector having a largest eigenvalue by comparing the pre-collected arm motion data and the arm motion data currently being acquired. Here, the walking assist controller 223 may determine the left/right assist strength of the assist torque profile based on the set walking direction.

Figure 8:
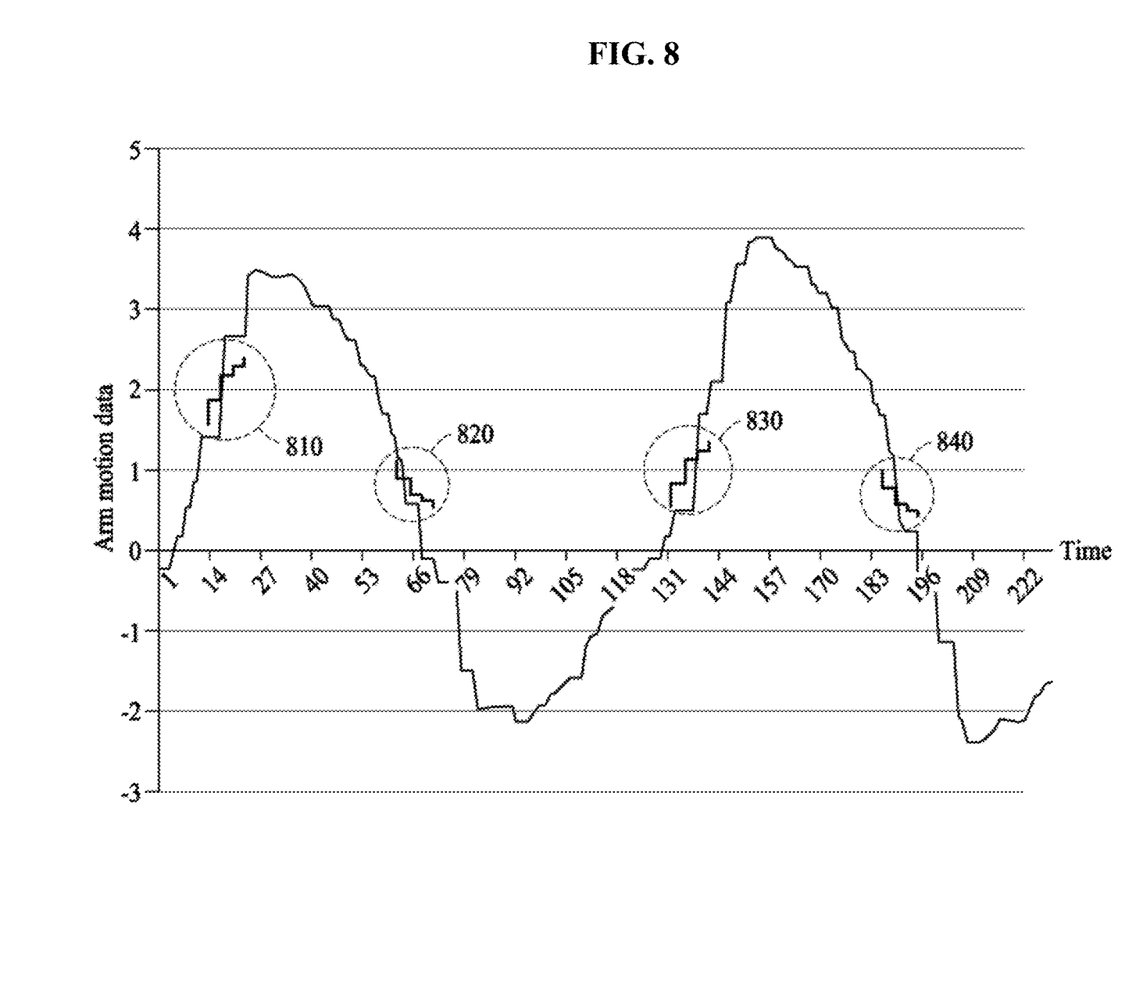
FIG. 8 illustrates an example of an operation of updating, at the walking assist controller of FIG. 5, arm motion data using a gyro modulation according to at least one example embodiment.
Figure 9A:
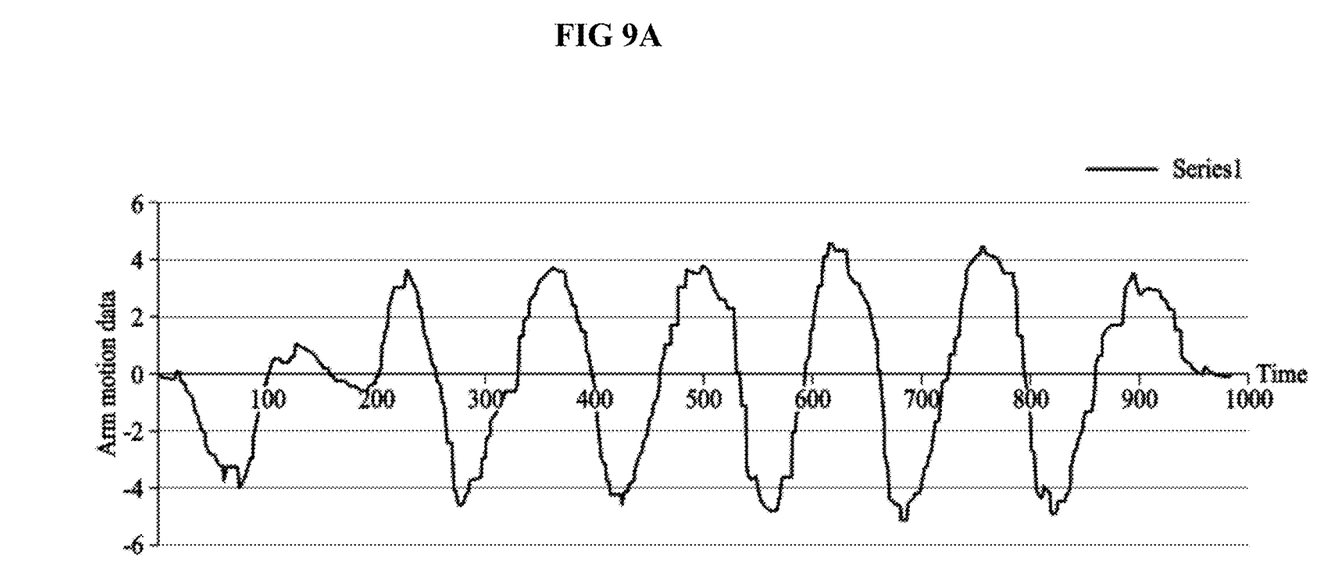
FIGS. 9A and 9B illustrate graphs before and after updating arm motion data using a gyro modulation as one example of an updating operation according to at least one example embodiment.
Figure 9B:
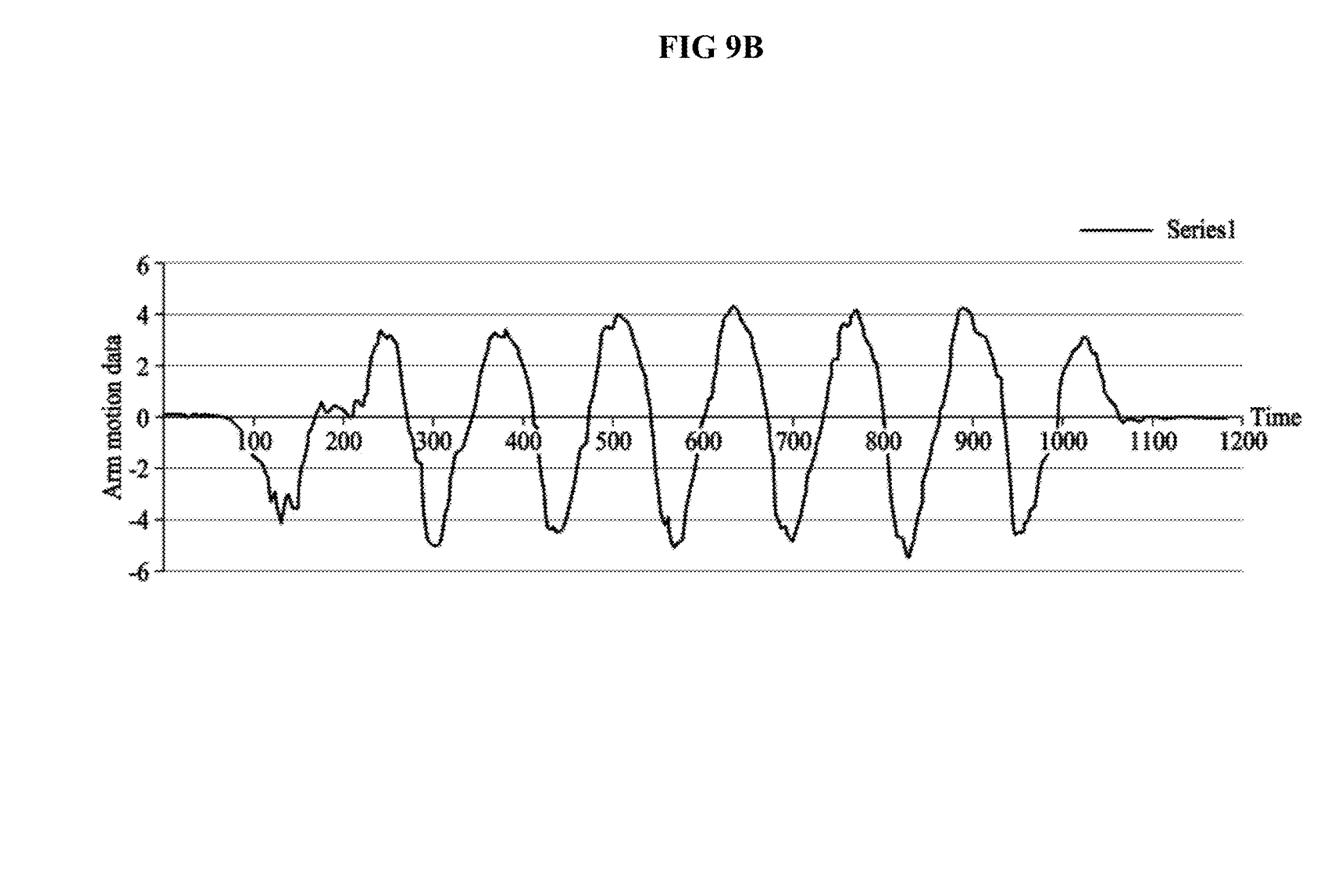

FIG. 8 illustrates an example of an operation of updating, at the walking assist controller 223 of FIG. 5, the arm motion data using a gyro modulation according to at least one example embodiment, and FIGS. 9A and 9B illustrate graphs before and after updating the arm motion data using a gyro modulation as one example of an updating operation according to at least one example embodiment.

Referring to FIG. 8 and FIGS. 9A and 9B, the walking assist controller 223 may update the arm motion data using a gyro modulation. For example, during communication between the electronic device 100 and the walking assist device 200, a wireless communication delay may occur and/or data transmission may not be properly performed. Here, the walking assist device 200 may use previous data alike. If new data is acquired, arm motion data may include step-shaped data 810, 820, 830, and 840.

The step-shaped data 810, 820, 830, and 840 may be discontinuous data in continuous data in a case in which a relatively great change occurs in data during a relatively short time interval, a case in which a relatively small change occurs in data during a relatively great time interval, and the like. The step-shaped data 810, 820, 830, and 840 may cause unstable walking assist, which may cause the user 900 to have resistance and/or displeasure.

Accordingly, the walking assist controller 223 may compensate for and/or correct a delay to quickly reach new data from previous data in which the delay is present.

The walking assist controller 223 may correct the step-shaped data 810, 820, 830, and 840 through linear compensation using an average data value. Every time delay occurs, the walking assist controller 223 may store delay values and average delay values in a memory (not shown).

In some example embodiments, the walking assist controller 223 may correct the arm motion data according to Equation 1 based on the linear correction scheme.

$$gyro(n)=gyro(n-1)+(gyro'(n)+gyro(n-1))/T_D \quad \text{[Equation 1]}$$

In Equation 1, gyro(n) denotes n-th arm motion data, gyro'(n) denotes n-th arm motion data received at the walking assist device 200, and $T_D$ denotes an average delay time. Also, if the walking assist device 200 starts an operation, no data may be accumulated. Thus, n denotes an integer greater than or equal to 2, and gyro(1)=gyro'(1).

In other example embodiments, the walking assist controller 223 may correct the step-shaped data 810, 820, 830, and 840 using the gyro modulation. The gyro modulation may be a data modulation scheme based on a difference of gyro data. The walking assist controller 223 may correct the arm motion data according to Equation 2.

$$gyro(n)=gyro(n-1)+(gyro'(n)+gyro(n-1))/2 \quad \text{[Equation 2]}$$

In Equation 2, gyro(n) denotes n-th arm motion data, and gyro'(n) denotes n-th arm motion data received at the walking assist device 200. Also, if the walking assist device 200 starts an operation, no data may be accumulated. Thus, n denotes an integer greater than or equal to 2, and gyro(1)=gyro'(1).

An example of applying, at the walking assist controller 223, the gyro modulation to the arm motion data being acquired may be represented as shown in Table 1.

TABLE 1

| gyro'(n) | 2 | 3 | 3 | 3 | 4 | 4 |
|---|---|---|---|---|---|---|
| gyro(n) | 2 | 2.5 | 2.75 | 2.875 | 3.4375 | 3.71875 |

Examples of updating, at the walking assist device 200, arm motion data using the gyro modulation may be represented as shown in FIGS. 9A and 9B. In detail, FIG. 9A shows an example of arm motion data acquired at the walking assist controller 223 and FIG. 9B shows an example of applying, at the walking assist controller 223, the gyro modulation to arm motion data. Referring to FIGS. 9A and 9B, the walking assist controller 223 may correct step-shaped data of the arm motion data by applying the gyro modulation to the arm motion data, and the walking assist device 200 may transfer a stable and smooth power to the user 900.

Figure 10:
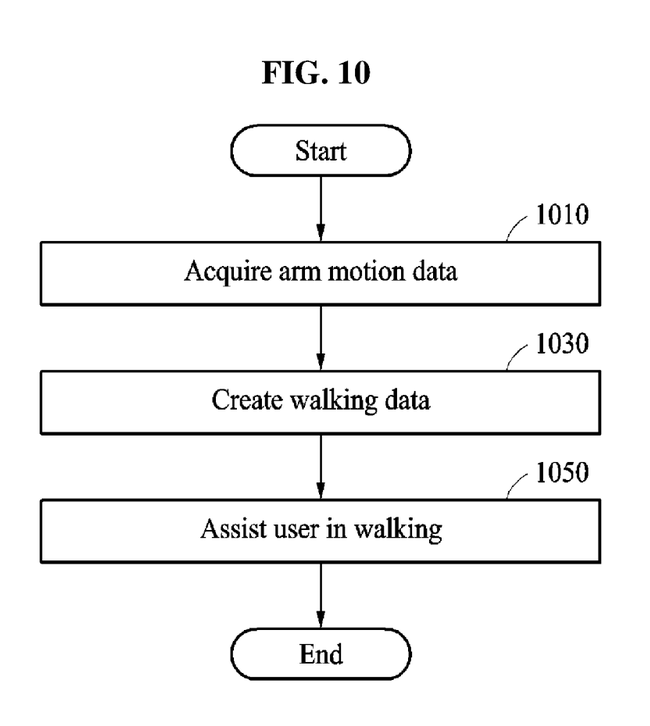
FIG. 10 illustrates a walking assist method performed at a walking assist device according to at least one example embodiment.

FIG. 10 illustrates a walking assist method performed at a walking assist device according to at least one example embodiment.

Referring to FIG. 10, in operation 1010, the walking assist device 200 may acquire the arm motion data. The arm motion data may include acceleration data and gyro data according to a motion of an arm of the user 900. The walking assist device 200 may acquire the arm motion data from the electronic device 100.

In operation 1030, the walking assist device 200 may generate the walking data based on the arm motion data. The walking data may be data used to assist the user 900 in walking and/or exercise. The walking data may include an assist torque profile.

In operation 1050, the walking assist device 200 may assist the user 900 in walking based on the walking data. The walking assist device 200 may transfer an assist force or an assist torque to the user 900 to assist the user 900 in walking and/or exercise.

The units and/or modules described herein may be implemented using hardware components and software components. For example, the hardware components may include microphones, amplifiers, band-pass filters, audio to digital convertors, and processing devices. A processing device may be implemented using one or more hardware device configured to carry out and/or execute program code by performing arithmetical, logical, and input/output operations. The processing device(s) may include a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

The software may include a computer program, a piece of code, an instruction, or some combination thereof, to independently or collectively instruct and/or configure the processing device to operate as desired, thereby transforming the processing device into a special purpose processor. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A method of assisting a walking operation, the method comprising:
   acquiring, by a controller, arm motion data;
   generating, by the controller, walking data based on the arm motion data, the generating including,
   extracting a plurality of direction vectors from the arm motion data,
   classifying the plurality of direction vectors into a first group and a second group based on a direction,
   determining a first representative direction vector associated with the first group based on an average of the plurality of direction vectors associated with the first group,
   determining a second representative direction vector associated with the second group based on an average of the plurality of direction vectors associated with the second group, and
   generating the walking data by performing an inner product on the first representative direction vector and the arm motion data, and by performing an inner product on the second representative direction vector and the arm motion data; and
   generating, by the controller, an assist torque profile to assist the walking operation based on the walking data.

2. The method of claim 1, wherein the generating comprises:
reduce noise from the arm motion data, the noise being one or more of greater than a high threshold and less than a low threshold.

3. The method of claim 1, wherein the generating comprises:
reduce high frequency data from the arm motion data by filtering the arm motion data based on at least one of norm data and a magnitude of a vector.

4. The method of claim 1, wherein the acquiring comprises:
acquiring the arm motion data using at least one of a gyro sensor and an accelerometer sensor.

5. The method of claim 4, wherein the at least one of the gyro sensor and the accelerometer sensor is included in a portable electronic device.

6. The method of claim 1, wherein the generating comprises:
determining a magnitude of the walking data based on norm data associated with the arm motion data.

7. The method of claim 1, wherein the generating comprises:
generating the walking data by comparing a first eigenvalue of pre-collected arm motion data and a second eigenvalue of the arm motion data, the first eigenvalue and the second eigenvalue being created through a principle component analysis (PCA).

8. The method of claim 1, further comprising:
updating, by the controller, the arm motion data using a gyro modulation calculated using:

$$\mathrm{gyro}(n)=\mathrm{gyro}(n-1)+(\mathrm{gyro}'(n)+\mathrm{gyro}(n-1))/2$$

where n denotes an integer greater or equal to 2, gyro(n) denotes updated n-th arm motion data, gyro'(n) denotes n-th arm motion data received at a walking assist device, and gyro(1)=gyro'(1).

9. The method of claim 1, further comprising:
generating, by a driver, an assist force or an assist torque based on the assist torque profile.

10. A walking assist device comprising:
a receiver configured to acquire arm motion data; and
a controller configured to,
generate walking data based on the arm motion data by,
extracting a plurality of direction vectors from the arm motion data,
classifying the plurality of direction vectors into a first group and a second group based on a direction,
determining a first representative direction vector of the first group based on an average of the plurality of direction vectors associated with the first group,
determining a second representative direction vector associated with the second group based on an average of the plurality of direction vectors associated with the second group,
generating the walking data by performing an inner product on the first representative direction vector and the arm motion data, and by performing and inner product on the second representative direction vector and the arm motion data, and
generating an assist torque profile to assist a walking operation based on the walking data.

11. The walking assist device of claim 10, wherein the controller is further configured to reduce noise from the arm motion data, the noise being one or more of greater than a high threshold and less than a low threshold.

12. The walking assist device of claim 10, wherein the controller is further configured to reduce high frequency data from the arm motion data by filtering the arm motion data based on at least one of norm data and a magnitude of a vector.

13. The walking assist device of claim 10, wherein the arm motion data includes at least one of angular velocity data generated by a gyro sensor and acceleration data generated by an accelerometer sensor.

14. The walking assist device of claim 13, wherein the at least one of the gyro sensor and the accelerometer sensor is included in a portable electronic device.

15. The walking assist device of claim 10, wherein the controller is further configured to determine a magnitude of the walking data based on norm data associated with the arm motion data.

16. The walking assist device of claim 10, wherein the controller is further configured to generate the walking data based on a first eigenvalue of pre-collected arm motion data and a second eigenvalue of the arm motion data, the controller configured to generate the first eigenvalue and the second eigenvalue through a principle component analysis (PCA).

17. The walking assist device of claim 10, wherein the controller is further configured to update the arias motion data using a gyro modulation calculated using:

$$\mathrm{gyro}(n)=\mathrm{gyro}(n-1)+(\mathrm{gyro}'(n)+\mathrm{gyro}(n-1))/2$$

where n denotes an integer greater or equal to 2, gyro(n) denotes updated n-th arm motion data, gyro'(n) denotes n-th arm motion data received at the walking assist device, and gyro(1)=gyro'(1).

18. The walking assist device of claim 10, further comprises a driver configured to generate an assist force or an assist torque based on the assist torque profile.

* * * * *